United States Patent [19]

Rainer et al.

[11] Patent Number: 4,801,579
[45] Date of Patent: Jan. 31, 1989

[54] NOVEL CYSTINE COMPOUNDS, THEIR PREPARATION AND USE

[75] Inventors: Naderer Rainer, Arnoldstein; Buxbaum Lothar, Villach, both of; Langer Klaus, Erlangen, Fed. Rep. of Germany

[73] Assignees: Bleiberger Bergwerks Union, Austria; Pfrimmer & Co. Pharmazeutische Werke Erlangen GmbH & Co. KG, Fed. Rep. of Germany

[21] Appl. No.: 115,796

[22] Filed: Nov. 2, 1987

[30] Foreign Application Priority Data

Nov. 7, 1986 [AT] Austria .................................. 2980/86

[51] Int. Cl.$^4$ ...................... A61K 37/00; C07C 103/00
[52] U.S. Cl. ......................................... 514/18; 514/19; 530/531; 540/454; 548/535; 562/557
[58] Field of Search ................ 562/557; 530/331; 548/535; 540/454; 514/18, 19

[56] References Cited

U.S. PATENT DOCUMENTS 3,875,136  4/1975  Kamber .............................. 260/112.5
4,325,943  4/1982  Natarajan ............................ 424/177

FOREIGN PATENT DOCUMENTS 0195356  8/1987  Japan .

Primary Examiner—Paul Lieberman
Assistant Examiner—Kathleen Markowski
Attorney, Agent, or Firm—Beveridge, DeGrandi & Weilacher

[57] ABSTRACT

Novel cystine compounds of the general formula I are proposed wherein the AS independently of one another each represent a, preferably natural, L-amino acid, in particular glycine, alanine, proline, threonine, serine, valine, arginine, lysine or ornithine; the $R_1$ independently of one another each stand for an acyl group of an organic acid with 2 to 5 carbon atoms, preferably for acetyl-, propionyl-, succinyl- or hydroxysuccinyl- or for a, preferably natural, L-amino acid which via its carboxylic group is linked amide-like to the amino group of the amino acid AS, the amino acids indicated as preferred for AS also being preferred for the amino acids of $R_1$, or the two $R_1$ together form the acyl group of an organic dicarboxylic acid, preferably the succinic or malic group; and the $R_2$ independently of one another each are an alkoxy group with 1 to 4 carbon atoms, preferably methoxy or ethoxy, the hydroxy group, where in case of the meaning of $R_2$=OH the carboxylic group(s) are each present as such or as an inorganic or organic salt, preferably with NaOH or KOH, organic bases or basic amino acids such as L-lysine, L-ornithine, L-arginine or L-histidine, or the radical of a further amino acid bound via an amide group, the carbocylic group(s) of the amino acid optionally also having the form of an inorganic or organic salt; further processes for their preparation as well as nutrient compositions formed therewith.

14 Claims, No Drawings

NOVEL CYSTINE COMPOUNDS, THEIR PREPARATION AND USE

The present invention relates to novel cystine compounds, their production and use, above all as a component of nutrient compositions.

For maintaining the vital functions of man and mammals, the organisms must be supplied, a.o., with protein-containing nutrients which are converted to amino acids by the digestive system. The amino acids formed are used by the body for growth, development, cell propagation and metabolic functions.

At failure or defects of the digestive system or in patients excessively weakened by various influences such as the after-effects of accidents or surgery, but also in the case of specific disorders such as chronic kidney failure or liver insufficiency which require the supply of amino acids by far exceeding the normal extent, free amino acids must be administered orally by means of appropriate preparations.

In many instances, however, the oral administration of nutrients is impossible or difficult. This particularly applies after surgery, in severe cancer cases, burns, infections, kidney failure, liver insufficiency, prolonged unconsciousness and severe metabolic disorders. In cases of this type, the patients must be fed parenterally by means of infusion solutions particularly containing amino acids in a suitable ratio in addition to carbohydrates and fats. In addition to the amino acids considered essential such as lysine, leucine, isoleucine, tryptophane, methionine, valine, phenylalanine and threonine, certain groups of persons absolutely need the supply of further amino acids.

For newborns and infants as well as for patients with certain diseases (such as cirrhosis of the liver), for instance, the amino acid cysteine, for instance its oxidized form (cystine) is an essential amino acid—which means that it cannot be formed by the organism from the amino acid methionine, but must be supplied to the organism directly as such. The amino acid L-cysteine is well soluble in water (about 16 g/100 g water), but is not resistant to heat treatment, so that cysteine-containing solutions cannot be sterilized without the decomposition of the cysteine. The amino acid L,L-cystine (which can be utilized by the body just like L-cysteine) is stable against heat treatment, but sparingly soluble in water (0.0095 g/100 g water), so that it is not suitable for use in a solution for parenteral nutrition.

Attempts at increasing the water solubility of cystine have resulted in the formation of various dipeptides and tripeptides, although these are unsuitable for the conventional preparation of infusion solutions due to their low thermal stability. Some of them are of little practical use because of their complicated structure and difficult purification.

The search for cystine derivatives suitable as the components of nutrient compositions has resulted in a group of new compounds of the general formula

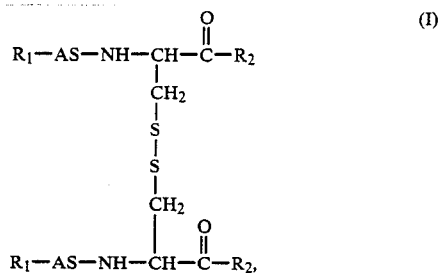

wherein AS independently of one another each represent a, preferably natural, L-amino acid, in particular glycine, alanine, proline, threonine, serine, valine, arginine, lysine or ornithine; $R_1$ independently of one another each mean an acyl group of an organic acid with 2 to 5 carbon atoms, preferably acetyl, propionyl, succinyl or hydroxysuccinyl or for a preferably natural L-amino acid which is via its carboxylic group linked amide-like to the amino group of the amino acid AS, with the preferred amino acids mentioned for AS also preferred for the amino acids of $R_1$, or the two $R_1$ together forming the acyl group of an organic dicarboxylic acid, preferably the succinic or malic group; and $R_2$ independently of one another each standing for an alkoxy group with 1–4 carbon atoms, preferably for methoxy or ethoxy, for the hydroxy group, in case of $R_2$=OH, any carboxyl group(s) being present as such or in the form of an inorganic or organic salt, preferably with NaOH or KOH, organic bases or basic amino acids such as L-lysine, L-ornithine, L-arginine or L-histidine, or the radical of a further amino acid bound via an amide group, their carboxylic group(s) optionally being present in the form of an inorganic or organic salt.

It was surprisingly found that compounds of this group, in particular bis-(acetylglycyl)-L,L-cystine and its salts, are well soluble in water and stable enough to be heat-sterilizable (for instance by heating to 120° C. for 5 minutes).

The novel compounds of the formula I thus represent valuable components of a nutrient composition, on the one hand, and permit the simple sterilization thereof, on the other hand.

The novel compounds are basically prepared by peptide syntheses and acylation; for instance L,L-cystine, an L,L-cystine alkyl ester or an L,L-cystine peptide in which an amide bridge to a further amino acid is formed on at least one carboxylic group of the L,L-cystine can be subjected to peptide coupling with at least one α-aminoacylated amino acid via the α-amino groups of the L,L-cystine derivative.

On the other hand, the cystine peptide formed with an α-amino-unsubstituted amino acid can be α-aminoacylated subsequently.

The following are examples of peptide coupling processes:

(a) Activated Ester Process

The α-aminoacylated amino acid is reacted with 4-nitrophenol in the presence of dicyclohexyl carbodiimide as a water-removing reactant in a suitable solvent (acetonitrile, tetrahydrofurane or dimethyl formamide). After a reaction time of 2 to 96 hours, the urea formed is filtered off and the 4-nitrophenyl ester is isolated following evaporation of the solvent.

The activated ester thus obtained is coupled with L,L-cystine in the presence of caustic soda in a suitable solvent (e.g. dimethyl formamide, acetonitrile, tetrahydrofurane) to form the peptide with in 2 to 96 hours. Following acidification by means of a suitable acid (hydrochloric acid or sulphuric acid) the solvent is evaporated. The residue is distributed over two immiscible solvents (such as water and acetic acid ethyl ester) in order to remove the 4-nitrophenol formed. After evaporation of the water, the final product is isolated from the aqueous phase and purified by recrystallization in a suitable solvent (e.g. dimethylformamide, water, ethanol).

(b) Azlactone Process

The α-aminoacylated a-mino acid is condensed in a suitable solvent (e.g. dimethylformamide) with a water-removing reactant (e.g. dicyclohexyl carbodiimide, acetic acid anhydride) to form 2-alkyl-1,3-oxazoline-5-one. In the case of acetic acid anhydride, the solvent may be omitted so that the acid anhydride itself acts as the solvent. After a reaction time of 1 to 96 hours, the urea optionally formed is filtered off and the solvent is subsequently evaporated. The residue is purified by recrystallization in a suitable solvent (e.g. ethanol). The azlactone obtained is reacted with the sodium salt of L,L-cystine in a suitable solvent (e.g. tetrahydrofurane, dimethylformamide, acetonitrile). After a reaction time of 1 to 96 hours, the peptide is liberated by acidification by means of a suitable acid such as hydrochlorid acid or sulphuric acid. Following evaporation of the solvent, the peptide is separated from the inorganic components by extraction with a suitable organic solvent such as ethanol. Following the evaporation of the solvent, the peptide is purified by recrystallization in a suitable solvent.

(c) The α-aminoacylated amino acid can be directly converted to the respective peptide by condensation with L,L-cystine diester in the presence of a water-removing reactant (e.g. dicyclohexyl carbodiimide).

(d) The α-aminoacylated amino can be converted to the acid chloride, acid anhydride or acid azide which is then reacted with L,L-cystine or the corresponding ester to form the peptide.

The acylation of an L,L-cystine peptide already formed on the α-amino positions is explained by means of the example of the preparation of bis-(acetylglycyl)-L,L-cystine from the tripeptide bis-glycyl-L,L-cystine: the tripeptide is dissolved in an equimolar amount of aqueous base and then an appropriate molar amount of acetic acid anhydride is added under cooling, an appropriate amount of base is added in order to bind the acetic acid liberated during the reaction. After completion of the reaction, the peptide is liberated by the addition of an appropriate amount of acid (for instance hydrochloric acid or sulphuric acid). Following the evaporation of the water, the acylated peptide is separated by extraction with a suitable solvent (e.g. ethanol, acetone). The crude peptide obtained after evaporation of the solvent is purified by recrystallization from a suitable solvent (e.g. ethanol, acetone, dimethylformamide, acetonitrile, water) or combinations thereof.

All usual acylating agents, a.o. substances such as acetic acid-4-nitrophenyl ester or thioacetic acid, are suitable.

The process for the preparation of the novel compounds of the formula I is thus characterized in that in a solvent as well as in the presence or absence of a base, L,L-cystine or an in particular carboxyl-substituted, cystine derivative, is reacted (a) with an activated ester of an acylated amino acid,
(b) with a 1,3-oxazoline-5-one-derivative (azlacton) substituted in 2-position by an alkyl, aryl, alkaryl or aralkyl,
(c) with an acylated amino acid in the presence of a water-removing reactant, for instance in the presence of dicyclohexyl carbodiimide or ethoxy acetylene, or
(d) with an acid chloride, acid anhydride or azide of an acylated amino acid, or an N,N'-bis-amino acid-L,L-cystine derivative is acylated in at least one α-amino group and the compounds of the formula I thus obtained are optionally converted to salts by means of at least one component of the group consisting of inorganic and organic bases as well as basic amino acids.

When the novel compounds of the formula I are used as components of nutrient compositions, they are formulated in the manner usual in the pharmaceutical field for the preparation of solid and liquid preparations or preparations with liquid content such as capsules.

So, for instance, infusion solutions are prepared by dissolving the purified peptide and the desired amino acid in distilled water. Mineral salts and other substances may further be added to these solutions. Prior to administration, they must be isotonically adjusted. Up to now, it has not been possible to sterilize such solutions in the usual manner (5 minutes, 120° C., pH 5.5 to 7.5) without the decomposition of the cystine-containing component. The novel peptides according to the invention permit a heat treatment of the above-mentioned infusion solution without the decomposition of the cystine derivative.

When these infusion solutions are used together with carbohydrates (e.g. glucose), the carbohydrate and amino acid solutions must be sterilized separately as otherwise a Maillard reaction (and subsequent discoloration) would set in.

The cystine derivatives described are also suitable for the preparation of orally administered amino acid preparations such as tablets, granules, lozenges or capsules, for instance capsules filled with oil phase.

In the following, some examples for the preparation and testing of the cystine peptide derivatives according to the invention are given:

EXAMPLE 1

Synthesis of bis-(benzyloxycarbonylglycyl)-L,L-cystine 35.3 g of L,L-cystine (0.147 mol) were dissolved in 340 ml 1N caustic soda, cooled to less than +10° C. and a solution of 90 g n-benzyloxycarbonylglycine hydroxysuccinimide ester (0.294 mol) in 350 ml acetone was added dropwise. After a total reaction period of 12 h, the acetone is removed by evaporation in vacuo. The product is liberated by acidification by means of diluted sulphuric acid; it is extracted by means of an organic solvent and recrystallized from a suitable solvent mixture.

Yield: 60 g (65% theory)

m.p.: 135°–140° C.

TLC (thin layer chromatography) (n-butanol/glacial acetic acid/water 60/30/30): $R_f=0.6$ (n-propanol/ammonia 2/1): $R_f=0.7$

EXAMPLE 2

Synthesis of bis-glycyl-L,L-cystine 125 ml 33% hydrobromic acid in glacial acetic acid are poured over 50 g bis-(benzyloxycarbonylglycyl)-

L,L-cystine (0.08 mol). After 1 hour stirring, 1 l diethyl ether is added and left standing under cooling for crystallization. The crystalline precipitate is filtered off and washed free of benzyl bromide by means of diethyl ether. The dried product is dissolved in water and the peptide is liberated from the hydrobromide by the addition of a base. After removal of the solvent, the product is purified by treatment with an organic solvent (e.g. dimethylformamide, acetonitrile, methanol).

Yield: 22 g (70% theory)
$[\alpha]^{20D}$: $-116°$ (C=1 in water)
TLC (n-butanol/glacial acetic acid/water 60/30/30): $R_f=0.1$ (n-propanol/ammonia 2/1): Rf=0.05

EXAMPLE 3

Synthesis of bis-(acetylglycyl)-L,L-cystine 3.5 g bis-glycyl-L,L-cystine (0.01 mol) are dissolved in 20 ml 1N caustic soda and cooled to less than +10° C.; at the same time, 3.1 g acetic anhydride (0.03 mol) and 55 ml 1N caustic soda are added. After a total reaction time of 2 hours, the pH is adusted to 1-2 by the addition of acid. Following evaporation of the water in vacuo, the product is separated from the inorganic salt by extraction with a suitable organic solvent (e.g. an alcohol). After removal of the solvent in vacuo, the residue is recrystallized from ethanol/acetone.

Yield: 3.1 g (70% theory)
m.p.: 124°-134° C.
$[\alpha]_{20}{}^D$: $-124.5°$ (C=1 in water)
TLC (ethanol/water 9/1): $R_f=0.67$

EXAMPLE 4

Testing of the water solubility and thermal stability of bis-(acetylglycyl)-L,L-cystine 0.5 g bis-(acetylglycyl)-L,L-cystine are dissolved in 50 ml distilled water. The pH is adjusted to 6.5 by the addition of a 1N sodium hydrogen carbonate solution and then diluted with distilled water to a volume of 100 ml. Of this solution, an HPLC chromatogram is made immediately. The solution is then heated on a boiling water bath. The HPLC chromatogram does not show any essential changes after 10, 20 and 30 minutes of heating respectively.

EXAMPLE 5

The ingredients indicated in the following table were dissolved in distilled water and filled into infusion bottles. These were subsequently sterilized.

| Peptide and amino acids | g/1000 ml |
|---|---|
| bis-(acetylglycyl)-L,L-cystine | 1.4 |
| L-isoleucine | 2.5 |
| L-leucine | 2.8 |
| L-lysine | 1.5 |
| L-methionine | 0.8 |
| L-phenylalanine | 1.4 |
| L-threonine | 1.7 |
| L-tryptophane | 0.56 |
| L-valine | 2.1 |
| L-arginine | 3.5 |
| L-histidine | 0.7 |
| L-alanine | 5.5 |
| L-asparagine | 4.0 |
| glycine | 0.5 |
| L-proline | 3.8 |
| L-ala-L-tyr (1) | 1.5 |

(1) dipeptide of L-alanine and L-tyrosine

EXAMPLE 6

Preparation of n-acetylglycine-4-nitrophenyl ester 29.3 g N-acetylglycine (0.25 mol) and 34.8 g 4-nitrophenol (0.25 mol) are dissolved in 250 ml dimethylformamide (DMF). Cooling to less than +10° C. is effected and 51.6 g dicyclohexyl carbodiimide (0.25 mol) are added. After a reaction period of 12 hours, the precipitated dicyclohexyl urea is filtered off and the DMF is evaporated in vacuo. The residue is recrystallized from a suitable solvent mixture (e.g. methanol/water or ethyl acetate/diethyl ether).

Yield: 38 g (64% theory)
m.pm: 120°-123° C.
TLC (ethanol/water): $R_f=0.8$

EXAMPLE 7

Preparation of bis-(acetylglycyl)-L,L-cystine dimethyl ester 9.5 g of n-acetylglycine-4-nitrophenyl ester (0.04 mol) and 6.8 g L,L-cystine dimethyl ester dihydrochloride (0.02 mol) are suspended in 100 ml DMF. After cooling to less than +10° C., 4.1 g triethylamine (0.04 mol) are added. After a 48 hour reaction period, the dimethylformamide is evaporated in vacuo. The product is recovered from the residue by extraction with a suitable organic solvent.

Yield: 5.6 g (50% theory)

EXAMPLE 8

Preparation of bis-(acetylglycyl)-L,L-cystine via 2-methyl-1,3-oxazolin-5-one (azlactone)

4.8 g of L.L-cystine (0.02 mol) are dissolved in 1N caustic soda. Then, 4 g of 2-methyl-1,3-oxazolin-5-one (0.04 mol) in an inert solvent are added dropwise. After 12 hours reaction time, acidification is effected and the solvent is removed in vacuo. The residue is recrystallized.

Yield: 5.7 g (65% theory)
Physical data: see example 3.

EXAMPLE 9

Preparation of bis-(acetylglycyl)-L,L-cystine dimethyl ester via carbodiimide 4.7 g acetylglycine (0.04 mol) are reacted with 6.8 g of L,L-cystine-dimethylester dihydrochloride (0.02 mol) in the presence of 8.3 g dicyclohexyl carbodiimide (0.04 mol) in DMF as the solvent.

The residue is recrystallized after filtering off the urea.

Yield: 5.3 g (60% theory)

EXAMPLE 10

Preparation of bis-(acetylglycyl)-L,L-cystine 36 g of L,L-cystine (0.15 mol) are dissolved in 300 ml water with 60.7 g triethylamine (0.6 mol).
64.3 g N-acetylglycine hydroxysuccinimide ester (0.3 mol) in dimethylformamide are added dropwise under cooling. After acidification, the solvent is removed and the residue is recrystallized.

Yield: 48.1 g (73% theory)
m.p.: 124°-134° C.
$[\alpha]_{20}{}^D$: $-124.5°$ (C=1 in water)
TLC (ethanol/water 9/1): $R_f=0.67$

EXAMPLE 11

Preparation of bis-(acetylglycyl)-4,6-cystine-bis-arginate

A 10% aqueous solution of bis-acetylglycyl-L,L-cystine is mixed with a 10% aqueous solution of L-arginine until the mixture reacts neutrally. The water is evaporated and the residue is purified by treatment with an organic solvent.

m.p.: 155°–165° C.
$[\alpha]_{20}{}^D$: −74.5° (C=1 in water)

EXAMPLE 12

Preparation of bis-acetyl-L-tyrosyl-L,L-cystine 2.27 g of bis-L-tyrosyl-L,L-cystine (0.004 mol) are suspended in water and a solution of 1.57 g acetic acid hydroxysuccinimide ester (0.010 mol) in dioxane is added dropwise. The pH value is kept constant between 6 and 10 by the addition of aqueous caustic soda. After acidification, the solvent is removed and the product obtained is recrystallized from water.

m.p.: 141°–146° C.
$[\alpha]_{20}{}^D$: −89.3° (C=1 in water)
TLC (ethanol/water 8/2): $R_f$=0.67

EXAMPLE 13

Preparation of bis-propionylglycyl-L,L-cystine 7.8 g bis-glycyl-L,L-cystine (0.02 mol) are dissolved in water and 0.9 mol of an organic base are added. 5.21 g (0.04 mol) of propionic acid anhydride are added dropwise under cooling.

Following acidification, the solvent is removed and the residue is recrystallized.

Yield: 8 g (86% theory)
m.p.: 133°–145° C.
$[\alpha]_{20}{}^D$: −128.8° (C=2 in 1N NaHCO₃)
TLC (ethanol/water 8/2): $R_f$=0.63

EXAMPLE 14

Preparation of bis-acetylglycyl-L,L-cystine dimethyl ester 3.4 g L,L-cystine dimethyl ester dihydrochloride (0.01 mol) and 13.3 g N-methyl morpholine (0.13 mol) are dissolved in ethanol. Then, 4.3 g acetylglycine hydroxysuccinimide ester (0.02 mol) are added under cooling. The solvent is removed and the residue is recrystallized from an organic solvent mixture.

m.p.: 155°–160° C.
$[\alpha]_{20}{}^D$: −92.5° (C=1 in water)
TLC (n-butanol/glacial acetic acid/water 2/1/1): $R_f$=0.45

EXAMPLE 15

Preparation of bis-acetyl-L-alanyl-L,L-cystine 6.9 g of bis-L-alanyl-L,L-cystine (0.018 mol) are suspended in 300 ml ethanol/water mixture. Then 6.1 g acetic acid hydroxysuccinimide ester (0.040 mol) dissolved in dioxane are added dropwise. The pH value is kept constant by the addition of caustic soda. After acidification, the solvent is removed and the product obtained is purified by recrystallization.

Yield: 6.2 g (84% theory)
m.p.: 194°–197° C.
$[\alpha]_{20}{}^D$: −181° (C=1 in water)
TLC (ethanol/water): $R_f$=0.42

EXAMPLE 16

Preparation of bis-glycylglycyl-L,L-cystine 11.7 g bis-glycyl-L,L-cystine (0.03 mol) are dissolved in water with 12.6 g sodium hydrogen carbonate (0.15 mol). Then, 16.3 g N-tert-butyloxycarbonylglycine hydroxysuccimimide ester (0.06 mol) are added under cooling in a suitable solvent. After a reaction period of 6 to 48 hours, acidification is effected and the solvent is removed. The residue is recrystallized from a solvent mixture. By the addition of trifluoroacetic acid, the tert-butyloxycarbonyl protection group is cleaved off and the peptide is liberated by the addition of ammonia.

Yield: 7.3 g (52% theory)
m.p.: 215°–218° C. (decomposition)
$[\alpha]_{20}{}^D$: −108.9° (C=1 in 1N HCl)

EXAMPLE 17

Preparation of bis-N-succinyl-glycyl-L,L-cystine 3.9 g bis-glycyl-L,L-cystine (0.01 mol) are dissolved in water, then a solution of 2.0 g succinic acid anhydride (0.02 mol) in a suitable solvent is added at constant pH value. After a reaction time of 1 hour, acidification is effected and the residue is recrystallized.

Yield: 5 g (90% theory)
m.p.: 105°–115° C.
$[\alpha]_{20}{}^D$: −88.5° (C=1 in water)
TLC (chloroform/methanol/glacial acetic acid 5/3/1): $R_f$=0.50

EXAMPLE 18

Preparation of bis-acetylglycyl-L,L-cystine-bis-L-tyrosine-ethylester salt

L-tyrosine ethylester hydrochloride is dissolved in water and the ester is liberated by the addition of sodium carbonate. The ester is taken up by a solvent (such as acetic acid ethyl ester). 8.9 g bis-acetylglycyl-L,L-cystine (0.02 mol) are dissolved in water and an equivalent amount of the organic solution of the tyrosine ethyl ester is added. The aqueous phase is washed with an organic solvent several times and the water is then evaporated. The residue is recrystallized from an organic solvent mixture.

Yield: 14.2 g (81% theory)
m.p.: 165°–170° C.
$[\alpha]_{20}{}^D$: −82.2° (C=1 in water)

We claim:

1. Cystine compounds of the general formula:

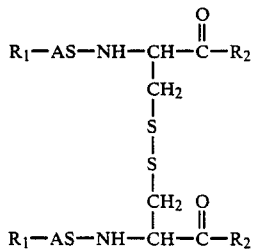

which compounds may be acids, esters or salts,
wherein the AS independently of one another represent a divalent entity of a natural, L-amino acid, a carboxyl group of said L-amino acid forming a peptide bond —CO—NH— together with the —NH group;

the $R_1$ independently of one another each stand for an acyl group of an organic acid with 2 to 5 carbon atoms or for a natural L-amino acid, a carboxylic group whereof forming a peiptide bond —CO—NH— together with an amino group of the amino acid AS, wherein the amino acids for which $R_1$ stands may be the same as the amino acids for AS or the two $R_1$ together may form the acyl group of an organic dicarboxylic acid; and when the compounds are acids, the $R_2$ independently of one another represents each an hydroxy group or $R_3$, wherein $R_3$ is a further amino acid, an amino group whereof forming a peptide bond —CO—NH— together with the

group, and when the compounds are esters, each of the $R_2$ independently represents an alkoxy group with 1 to 4 carbon atoms and when the compounds are salts $R_2$ is $OR_4$ or —$R_3R_4$, wherein $R_3$ has the above meaning and $R_4$, is the salt forming portion of a reactant member selected from the group consisting of inorganic bases, organic bases and basic amino acids.

2. A nutrient composition which contains at least one cystine compound as claimed in claim 1.

3. The nutrient composition as claimed in claim 2 further containing at least one member selected from the group consisting of polyols, fats, glucose, oligosaccharides, mineral salts, trace elements, vitamins and mixtures thereof.

4. The compounds according to claim 1, wherein AS represents a divalent entity of glycine, alanine, proline, threonine, serine, valine, arginine, lysine or ornithine and each $R_1$ stands for the acyl group of an organic acid with 2 to 5 carbon atoms.

5. The compounds according to claim 4, wherein each $R_1$ represents acetyl or propionyl.

6. The compounds according to claim 4, wherein each $R_1$ represents succinyl or hydroxysuccinyl or two $R_1$ together form succinyl or hydroxysuccinyl.

7. The compounds according to claim 1, wherein each $R_2$ represents an hydroxy group.

8. The compounds according to claim 1, wherein each $R_2$ represents —$OR_4$ or —$R_3R_4$, wherein $R_4$ is the salt forming portion of an organic base or of a basic amino acid.

9. The compounds according to claim 8, wherein each $R_4$ represents the salt forming portion of a basic amino acid selected from the group consisting of lysine, ornithine or arginine.

10. The compound as clamed in claim 1, which is bis-(acetylglycyl)-L,L-cystine, wherein each AS represents glycyl and wherein each $R_1$ is acetyl and each $R_2$ group is hydroxy.

11. The nutrient composition as claimed in claim 2 in which said at least one compound is present as an aqueous solution.

12. The nutrient composition as claimed in claim 11 which is an infusion solution, wherein the cystine compound is bis-(acetylglycyl)-L,L-cystine.

13. The nutrient composition according to claim 12 in which bis-(acetylglycyl)-L,L-cystine is present in a range of 0.1 to 20 percent based on the total composition.

14. The nutrient composition as claimed in claim 3 in which bis-(acetylglycyl)-L,L-cystine is in aqueous solution and is present in a range of 0.1 to 20 percent by weight based on the total composition.

* * * * *